(12) United States Patent  
Reisberg

(10) Patent No.: US 9,314,285 B2
(45) Date of Patent: Apr. 19, 2016

(54) MULTI-DIRECTIONAL THORAX WALL STABILISATION

(71) Applicant: MedXpert GmbH, Eschbach (DE)

(72) Inventor: Erhard Reisberg, Eschbach (DE)

( * ) Notice: Subject to any disclaimer, the term of this patent is extended or adjusted under 35 U.S.C. 154(b) by 221 days.

(21) Appl. No.: 14/130,377

(22) PCT Filed: Jun. 4, 2013

(86) PCT No.: PCT/EP2013/061446
§ 371 (c)(1),
(2) Date: Dec. 31, 2013

(87) PCT Pub. No.: WO2013/182545
PCT Pub. Date: Dec. 12, 2013

(65) Prior Publication Data
US 2014/0135853 A1    May 15, 2014

(30) Foreign Application Priority Data
Jun. 8, 2012    (DE) .......................... 10 2012 104 978

(51) Int. Cl.
| | |
|---|---|
| *A61B 17/04* | (2006.01) |
| *A61B 17/84* | (2006.01) |
| *A61F 2/08* | (2006.01) |
| *A61B 17/82* | (2006.01) |
| *A61B 17/80* | (2006.01) |

(52) U.S. Cl.
CPC ........... *A61B 17/823* (2013.01); *A61B 17/8076* (2013.01); *A61B 17/8085* (2013.01)

(58) Field of Classification Search
None
See application file for complete search history.

(56) References Cited

U.S. PATENT DOCUMENTS

| | | |
|---|---|---|
| 2004/0117016 A1 | 6/2004 | Abramson |
| 2006/0058786 A1 | 3/2006 | Kim et al. |
| 2008/0082101 A1* | 4/2008 | Reisberg ............ A61B 17/8076 606/60 |
| 2011/0034958 A1 | 2/2011 | Anderson et al. |

FOREIGN PATENT DOCUMENTS

| | | |
|---|---|---|
| DE | 195 20 464 | 2/1997 |
| DE | 10 2006 042277 | 3/2008 |
| DE | 11 2008 002 307 | 6/2010 |
| WO | 2012160109 | 11/2012 |

OTHER PUBLICATIONS

International Search Report, Dated Nov. 15, 2013, in PCT/EP2013/061446.

* cited by examiner

*Primary Examiner* — Sameh Boles
(74) *Attorney, Agent, or Firm* — Young & Thompson

(57) ABSTRACT

An implant (1) for attaching the first implant (1) to a tubular bone, in particular a rib bone, includes: a clamp (10) having a fillet (100) and prongs (101, 102, 103) extending from the fillet (100); and a first connecting element (11) for connecting the first implant (1) to a connector implant. The clamp (10) and the connecting element (11) are connected so as to be rotatable relative to each other about an axis.

17 Claims, 4 Drawing Sheets

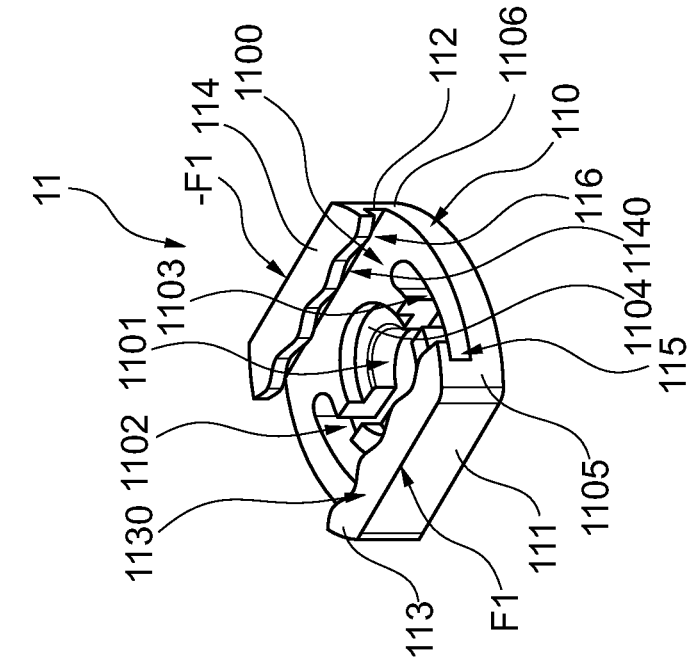
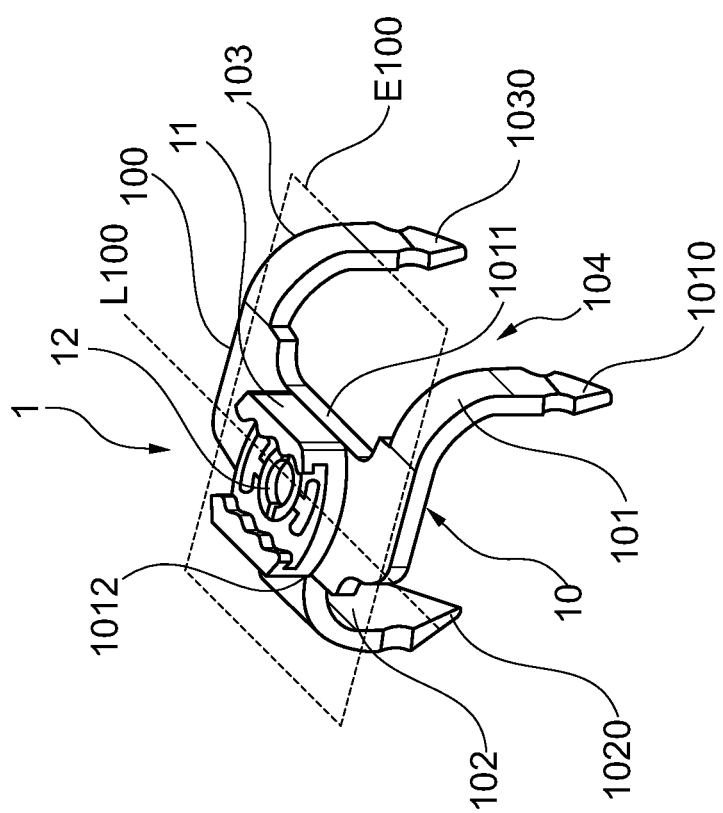

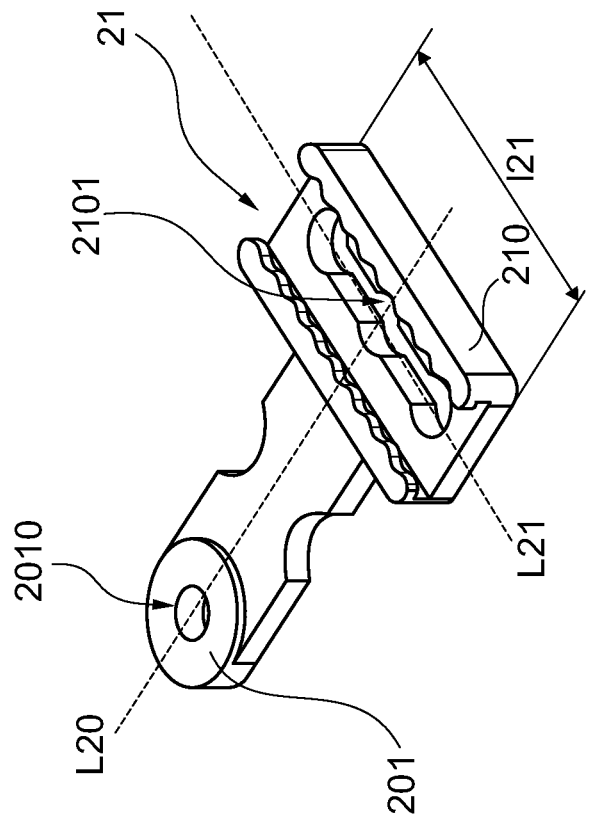
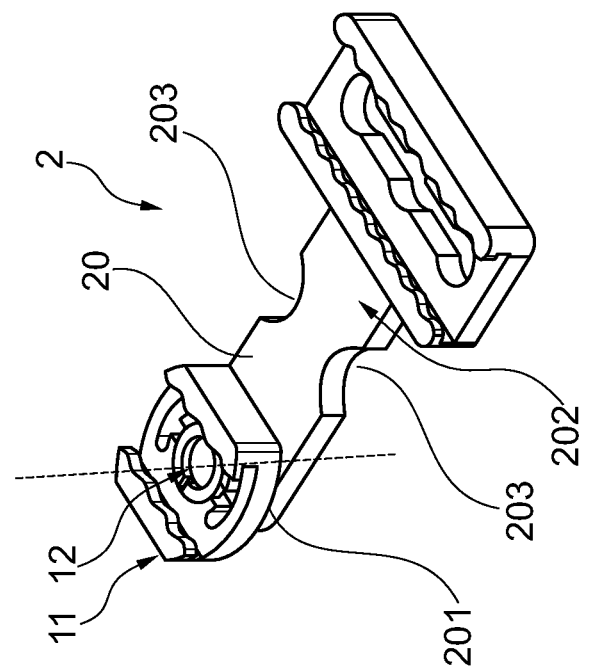
Fig. 6
Fig. 5

MULTI-DIRECTIONAL THORAX WALL STABILISATION

TECHNICAL FIELD

The present invention relates to a first implant for the attachment of the implant to a tubular bone, in particular a rib bone, comprising: a clamp having a fillet and prongs extending from the fillet; and a connecting element for connecting the implant to a connector implant. The present invention also relates to a first implant for the attachment of the implant to a tubular bone, in particular a rib bone, comprising: a clamp having a fillet which has a longitudinal axis and comprising at least a first prong, a second prong and a third prong, wherein the prongs extend from the fillet transversely to the longitudinal axis, and the first and third prongs are disposed relative to the longitudinal axis on a first side of the fillet, and the second prong is positioned relative to the longitudinal axis on a second side of the fillet. The invention also relates to a second implant for connecting two connector implants of an implant system, comprising: a fillet, a first connecting element and a second connecting element, wherein the first connecting element is disposed in a first end section of the fillet and the second connecting element is disposed in a second end section of the fillet.

PRIOR ART

During reconstructive and/or stabilising use of conventional implants on the bony thorax, long incisions or large-area preparations are required. This leads to considerable surgical trauma, and the patient must remain in the hospital for some time. The recovery phase is relatively long.

The prior art in deformities surgery today is that access to the bony thorax is gained by following the Ravitch procedure. In the vast majority of cases, deformities of the chest manifest themselves as Pectus excavatum, Pectus carinatum, Pectus arcuatum, etc. in the front area of the thorax, because malformations in the area of the anterior rib cartilage with impacts on the bony rib structures give rise to symmetrical or asymmetrical, at the very least cosmetically relevant, deformities.

Access to the anterior chest wall by following the Ravitch procedure consists in making a longitudinal axial incision with subsequent soft tissue preparation at the sternum or, transverse thereto, sub-mammary. The procedure is therefore relatively extensive and generally leaves a clearly visible scar.

OBJECT OF THE INVENTION

Proceeding therefrom, the object of the present invention is to provide an implant that supports minimally invasive reconstructive and/or stabilising procedures on the bony thorax, while allowing for versatile use of the implant for different anatomical conditions.

TECHNICAL SOLUTION

This object is achieved by a first implant in accordance with claim 1 or 5, and a second implant in accordance with claim 9. Advantageous embodiments are the object of the dependent claims.

In a first variant, the inventive first implant for attaching the implant to a tubular bone, in particular a rib bone, comprises: a clamp having a fillet and prongs extending from the fillet; and a connecting element for connecting the implant to a connector implant. In accordance with the invention, the clamp and the connecting element are connected relative to each other so as to rotate about an axis (or can be rotated or pivoted about the axis).

This ensures that the implant can be used in a versatile manner, i.e. in different conditions at different locations on the thorax. For example, if an attachment or anchorage for a connector implant, especially one that is rod-shaped, and/or a bridge are to be provided at a certain point on the thorax, the first step consists in attaching the clamp of the inventive first implant to a specific point on a rib bone. Subsequently, the connector implant and/or the bridge can be inserted into the connecting element. The connector implant is aligned relative to the connecting element in the longitudinal direction of the connecting element. In addition, the connecting element and thus the connector implant is aligned opposite the clamp at a specified desired angle and/or is rotated with respect to the clamp such that the connector implant can bridge a given section in the thorax area to a further attachment point in any direction. Whether the connecting element is immobilized at the desired angle at the clamp or remains rotatable depends on the requirements. In any case, the connector implant can be aligned multidirectionally relative to the clamp of the implant and be attached at any angle (relative to the clamp) to the connecting element. By moving the connector implant of the connecting element in a guide of the connecting element, the relative alignment of the connector implant along the longitudinal axis (or axial axis) of the connecting element can at the same time be adjusted and immobilized in the end position.

The outcome is that the connection between the connecting element (=shoe) and the fillet can be designed to rotate through 360 degrees so that connector implants may be aligned in any direction from one anchor point to the opposite anchor point.

Preferably, the implant has a connector which creates the rotatable connection between the clamp and the connecting element. Thus, the connector can be rotatably connected to the clamp and/or the connecting element. The connector can be attached (so as not to rotate) by press-fitting or screwing into the fillet and/or the connecting element, and the respective other component (connecting element or fillet) can be rotatably mounted to the connector. Thus, each component can have an opening through which is guided a base body of the connector which can be cylindrical or hollow-cylindrical and/or forms an axle. Detachment of the component rotatably attached to the connector from the connector and/or from the other component is prevented by an edge or projection, at least a section of which extends from the base body of the connector over the edge of the opening of the connector rotatably attached to the component.

Preferably, the clamp has a fillet which has a longitudinal axis and at least a first prong, a second prong and a third prong, wherein the prongs extend from the fillet transversely (especially perpendicularly) to the longitudinal axis, and the first and third prongs are disposed relative to the longitudinal axis on a first side of the fillet, and the second prong is disposed relative to the longitudinal axis on a second side of the fillet. The prongs are disposed in a staggered arrangement, relative to the longitudinal axis. In particular, the prongs are disposed in a staggered arrangement such that they are laterally offset from each other. In this way, the free ends of the prongs can engage with each other when compressed with a tool and do not hinder each other.

In a second variant, the inventive first implant for attaching the first implant to a tubular bone, in particular a rib bone, comprises: a clamp with a fillet, which has a longitudinal axis and at least a first prong, a second prong and a third prong, wherein the prongs extend from the fillet transversely, especially perpendicularly, to the longitudinal axis, and the first and third prongs are disposed relative to the longitudinal axis on a first side of the fillet, and the second prong is disposed relative to the longitudinal axis on a second side of the fillet. The prongs are disposed in a staggered arrangement, relative to the longitudinal axis. First and second side of the fillet generally lie opposite each other.

In particular, the prongs are disposed in a staggered arrangement such that they are laterally offset from each other. The first and third prongs can be disposed such that the second prong engages between them.

Especially, the sections of the prongs connected to the fillet extend transversely and/or perpendicularly outwards, relative to the longitudinal axis. The end sections of the prongs facing away from the fillet may also be bent down and out from a plane, which is determined by the fillet, such that the implant can be relatively easily applied to a rib bone and then the prongs can be bent at least partially around the rib bone by a tool. In this way, the fillet and prongs form a clamp.

Preferably, the thickness of the material of the second prong (along with the thickness of the material of any further prongs disposed on the second side and gripped by the tool) is set such that the resistance to bending corresponds to the sum of the resistance to bending of the first and the third prongs (together with the resistance to bending of any further prongs disposed on the first side and gripped by the tool). This prevents the clamp from rotating in the tool during attachment to the rib bone.

The range of clamp sizes to be offered can thus be kept to a minimum, a fact which is made possible by the "tongue and groove" concept of parallel lockable clamp prongs. The clamp is configured as a rule to have three offset prongs such that the prongs do not meet or overlap on the rear side of a rib where ribs are of different sizes, but can be immobilized side by side in parallel. Attachment to a rib bone is performed with a three-ended rib-clamp fixing tool having a three-piece jaw for gripping, guiding and bending the clamp.

With the aid of the variants of the first implant, it is possible, by making two small lateral incisions/preparations left and right of the sternum, to anchor the clamp implants to the ribs and by means of subsequent tunnelling to make room for the connecting fillet between the clamps. The idea of inserting implant bridges via several smaller accesses plus tissue tunnel could also be applied in an analogous way to other reconstructions/stabilisations of the thorax wall. The clamp implants can be anchored to a rib in the tightest of spaces.

Protection is claimed for different combinations of the characteristics mentioned and described in connection with the first variant of the inventive first implant and with the second variant of the inventive first implant, proceeding from the claimed basic form in each case, even if these combinations are not explicitly described.

The object is also achieved by a second implant for connecting two connector implants of an implant system, comprising: a fillet, a first connecting element and a second connecting element, wherein the first connecting element is disposed in a first end section of the fillet and the second connecting element is disposed in a second end section of the fillet. The first connecting element and/or the second connecting element is rotatably connected to the fillet.

The advantages of the rotatable attachment of a connecting element to the fillet were already described in connection with the first variant of the first implant. These advantages and possible applications are transferable to the second implant. In particular, multi-directional alignment of two connector implants with each other is possible. By moving the connector implants in a guide of the first and/or second connecting element, it is possible to simultaneously adjust the relative (axial or longitudinal) alignment of the respective connector implant with the corresponding connecting element and to immobilize it in its end position. The second implant, unlike the first implant, does not have an attachment clamp.

Preferably, the second implant has one connector per rotatable connection, said connector creating the rotatable connection between the fillet and the respective connecting element. Thus, the connector can be rotatably connected to the fillet and/or the respective connecting element. The connector can, for example, be attached (so as to not to rotate) by press-fitting or screwing into the fillet and/or the connecting element and the respective other component (connecting element or fillet) can be rotatably mounted to the connector. Thus, the respective component rotatably disposed on the connector can have an opening through which is guided a base body of the connector, which can be cylindrical or hollow-cylindrical and/or which forms an axle. Detachment of the rotatably mounted component in question from the connector and/or from the other component is prevented by an edge or projection, which extends from the base body of the connector toward the outside and at least partly over the edge of the opening.

The described second implant is a connecting member that, where an implant bridge is vertically aligned, supports a rigid angle-fixing or rotatable functionally dynamic interconnection of two connecting fillets to each other in the vicinity of the sternum or spine.

In particular, the connector of a first and second implant, as described above, is configured such that the fillet can be immobilized in any desired angular alignment relative to the connecting element. This variant is realized, for example, by a deformability of the connector, which can be formed, for example, as a hollow cylinder. Deformation occurs, for example, during immobilizing of a connector implant on the connecting element.

In an alternative embodiment, the connector is configured such that the connecting element retains a rotatable connection to the fillet when a connector implant is being immobilized on the connecting element. In this case, the connector is configured, for example, as a solid cylinder, which practically cannot deform under external forces of the kind that occur during immobilizing of the connector implant on the connecting element.

The invention also lays claim to implant systems consisting of at least two of the said implants (namely, first variant of the first implant, second variant of the first implant, second implant, and connector implant).

BRIEF DESCRIPTION OF DRAWINGS

Other features and advantages of the invention are apparent from the description of preferred embodiments according to the Figures.

FIG. 1 is a perspective view of a first embodiment of a first implant in accordance with the present invention;

FIG. 2 is a perspective view of a second component of the implant from FIG. 1;

FIG. 5 is a perspective view of an embodiment of a second implant in accordance with the present invention;

FIG. 6 is a perspective view of a first component of the second implant from FIG. 5;

DESCRIPTION OF PREFERRED EMBODIMENTS

Figure 4:
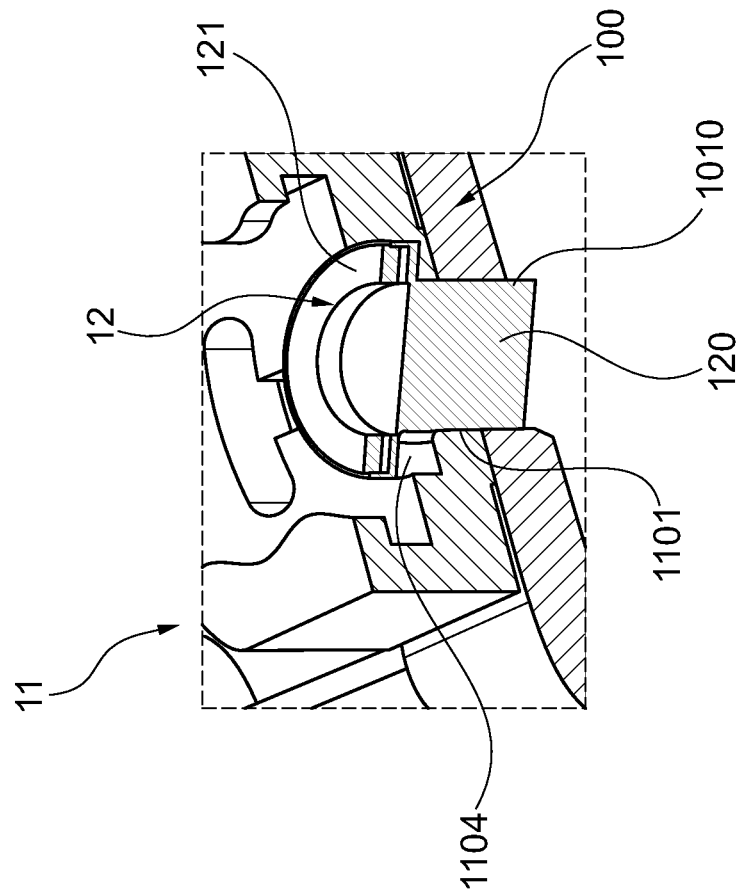
FIG. 4 is a lateral view of a detail of the implant from FIG. 1.

FIG. 1 shows a perspective view of a first embodiment of a first implant 1 in accordance with the present invention.

The first implant 1 has a clamp 10. This comprises a fillet 100 and prongs 101, 102, 103 extending from both sides of the fillet 100. The first prong 101 and the third prong 103 are (in the longitudinal direction L100 of the fillet) spaced apart from each other on a first side 1001 of the fillet 100, the second prong 102 is disposed on a second side 1002 opposite the first side 1001. The prongs 101, 102, 103 extend outwardly from the fillet 100 and roughly perpendicularly to the longitudinal axis L100 of the fillet 100 and are bent down and out from the plane E100 formed by the fillet 100. The prongs 101, 102 and 103 are disposed so as to be offset from one another on the fillet 100, relative to the longitudinal axis L100 of the fillet 100. In this connection, the second prong 102 is disposed at the level of the gap 104 between the first prong 101 and the third prong 103. The second prong 102 is disposed such that, when the free ends 1010, 1020, 1030 of the prongs 101, 102 and 103 are bent toward each other, it lies at the level of the gap 104 between the first prong 101 and the third prong 103 and/or engages with the gap 104.

The thickness of the material of the second prong 102 (in the present embodiment is determined by the width of the second prong; single prong) is greater than the thickness of the material of each of the first 102 and the third prong 103 (determined in the present embodiment by the width of each of the first prong 102 and/or the third prong 103; first prong 101 and third prong 103 form a double prong/arrangement of two prongs). The thicknesses and/or widths of the material are selected such that the sum of the resistances of the first and third prongs 101 and 103 is as large as the resistance of the second prong 102 when the first and third prongs 101 and 103 are bent by a tool toward the second prong 102 to firmly clamp the clamp 10 to a rib bone. This prevents the clamp 10 from tilting in the tool as the clamp 10 is being attached to the rib bone. The tool can especially be a bending pliers, whose number of jaw parts matches the number of prongs (in this case, a bending pliers with three jaw parts). In general, the sum of the resistance of the material of the prongs disposed on the first side is as great as the sum of the thicknesses/resistances of the material of the prongs disposed on the second side (insofar as the respective prongs are grasped by the tool). When a three-ended rib-clamp fixing-pliers is used, the resistance of the material of both sides (single prong and double prong arrangement, respectively) during bending is identical; uncontrolled tilting of the clamp in the jaw of the pliers is avoided. Further, a wider single prong is also advantageous because the area of contact on the rib is increased and better rotation stability is achieved.

By way of second component, the first implant 1 has a connecting element 11. This is configured for receiving and attaching a rod-shaped connector implant (not shown). In accordance with the invention, the connecting element 11 is rotatably attached to the fillet 100 so as to rotate about an axis A100, which is roughly perpendicular to the plane E100 formed by the fillet 100.

The rotatable connection between the fillet 100 of the clamp 10 and the connecting element 11 is created by means of a third component of the implant 1. The third component in the present embodiment is configured as a cylindrical connector 12. On one hand, this is immobilized in an opening of the fillet 100 and, on the other, it forms an axle to which the connecting element 11 is rotatably mounted.

In FIG. 2, the connecting element 11 is shown in more detail. The connecting element 11 has a base body 110 having a guide surface 1100, which is pierced by an opening 1101, a first aperture 1102 and a second aperture 1103. There is an annular groove 1104 on at least a section of that edge of the roughly cylindrical opening 1101 which is facing the guide surface 1100.

In addition, the connecting element 11 has a first guide bar 111, which extends upward from the guide surface 1100 along at least a section of a first side 1105 of the connecting element 11, and a second guide bar 112 which extends upward from the guide surface 1100 along at least a section of a second side 1106 of the connecting element 11. The guide bars 111 and 112 form lateral boundaries or guides for a guided and/or sliding connector implant 3 on the guide surface 1100 of the base body 110 (see FIG. 7).

At that side of the first guide bar 111 which is facing away from the guide surface 1100 is formed a first projection 113, which extends roughly parallel with the guide surface 1100 in the direction of the second guide bar 112. The free end 1130 of the first projection 113, which is facing the second guide bar 112, is provided with a tooth-like contour 1131.

Correspondingly, at that side of the second guide bar 112 which is facing away from the guide surface 1100 is formed a second projection 114, which extends roughly parallel with the guide surface 1100 in the direction of the first guide bar 111. The free end 1140 of the second projection 114, which is facing the first guide bar 111, is likewise provided with a tooth-like contour 1141. This means that the free ends of the first projection 113 and of the second projection 114 are opposite and aligned with each other. The tooth-like contours of the first projection 113 and of the second projection 114 too are thus opposite and facing each other.

The first guide bar 111 and the first projection 113 together form a first guide groove 115; the second guide bar 112 and the second projection 114 together form a second guide groove 116. Overall, the guide surface 1100, the bars 111, 112 and the projections 113, 114 form a guide in which a rod-shaped connector implant (not shown) with a dovetail-like structure can be guided parallel with the longitudinal axis 1110 of the base body 110, but is unable to perform any other translational and/or linear movements in other dimensions, relative to the connecting element 11.

When the projections 113 and 114 and thus the opposing tooth-like contours 115 and 116 are compressed, the base body 110 is deformed. This is facilitated inter alia by the apertures 1102 and 1103, which have a T-shape cross-section and which are each in communication with the opening 1101.

Figure 3:
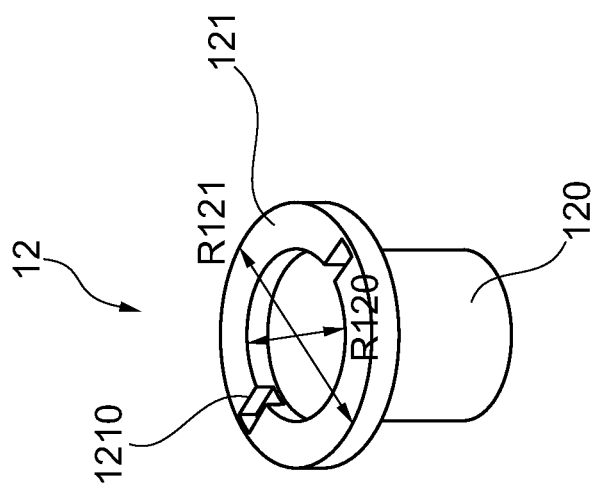
FIG. 3 is a perspective view of a third component of the implant from FIG. 1.

FIG. 3 shows by way of third component of the implant 1 the cylindrical connector 12, which connects the clamp 10 to the connecting element 11.

The cylindrical connector 12 has a base body 120 with a cylindrical outer surface. In the present embodiment, the base body 120 is cylindrical. However, it can alternatively be configured as a hollow cylinder or to be annular (not shown).

At a first end 1200 is formed a circular projection and/or edge 121 (R120<R121) extending outward beyond the radius R120 of the base body 120. At the side facing away from the base body 120 is formed a screw slot 1210 for firmly screwing the cylindrical connector 12 into the opening 1101 of the connecting element 11.

In the embodiment shown, when a connector implant in the connecting element is immobilized axially by compression of the guide bars, the rotatability of the connecting element is retained. This can be advantageous when a certain degree of flexibility of the support structure is desirable to take into account anatomical functional requirements (rotatable, functionally dynamic connection), for example, to facilitate the patient's breathing.

The connecting element, and thus the fillet connection can, in a different embodiment not shown, be immobilized in a defined alignment of the connecting element relative to the clamp (rigid, angle-fixing connection). To this end, the connector could, for example, have a hollow-cylindrical base body which, when a connector implant in the connecting element is immobilized axially by compression of the guide bars, is simultaneously deformed, i.e. is compressed in the opening and so loses its rotatability due to the deformation of the cylindrical base body.

FIG. 4 shows a cross-sectional view of a detail of the first implant 1. The cylindrical connector 12 is inserted into the opening 1101 of the connecting element 11, wherein the edge 121 engages with the groove 1104. As the outer contour of the base body 120 and of the edge 121 are circular in cross-section, the connecting element 11 is mounted so as to be rotatable about the axis A110 relative to and/or at cylindrical connector 12. The groove 1104 and the opening 1101 are configured so as to at least partially complement the outer contour of the base body 120 and/or of the edge 121, and so form a type of bearing for the cylindrical connector 12 (and/or the cylindrical connector forms a bearing for the connecting element).

On the other hand, that side of the base body 120 of the cylindrical connector 12 which is opposite the edge 121 engages with a mounting opening 1010 formed in the fillet 100 of the clamp 10 and is secured therein so as not to rotate, for example by press-fitting or screwing (in the latter case, the outer side of the base body 120 of the cylindrical connector 12 has an external thread which engages with a matching internal thread of the mounting opening 1010). However, the cylindrical connector 12 can also be rotatably connected to the clamp 10. If the components 10, 11 and 12 of the implant 1 are joined together, the connecting element 11 and the clamp 10 are in any case attached to one another so as to rotate relative to each other.

FIG. 5 shows a perspective view of an embodiment of a second implant 2 in accordance with the present invention.

The second implant 2 has a base body/fillet 20, in the first end section 201 of which is attached a first connecting element 11, as shown in FIG. 2 and described in that context. The connecting element 11 is attached to the base body 20 by means of a cylindrical connector 12, as shown in FIG. 4 and described in the context, so as to be rotatable about an axis A, which is (essentially) aligned perpendicularly to the surface of the base body 20.

The base body/fillet 20 extends along a longitudinal axis L20 (see FIG. 6) and has a first end section 201 and a second end section 202 opposite thereto. In the first end section 201 is formed an opening 2010 (corresponding to the opening 1010 in the first implant 1) in which is attached the cylindrical connector 12, as described in connection with the first implant 1.

Formed at the second end section 202 of the second implant 2 is a second connecting element 21, similar to the connecting element 11 described in connection with the first implant 1. To avoid unnecessary repetition, only the differences from the embodiment described in connection with FIG. 2 are presented. The second connecting element 21 is rigidly connected to the base body 20. Accordingly, it does not, unlike the first connecting element 11 from FIG. 2, have a central opening 1101 for engaging with a cylindrical connector 12. The base body 210, in contrast, has an aperture in 2101, the width of which varies along the longitudinal axis L210. This has the same function as the apertures 1102 and 1103 of the connecting element 1 described in connection with the first implant 11.

A recess 203 is formed roughly at the centre of the longitudinal axis L20 on both sides of the base body 20. The recesses (waists) 203 are located roughly in the centre of the fillet section and are intended to facilitate flexing during an operation without the use of tools.

Further, the second connecting element 21 extending transversely to the base body/fillet 20 has a length L21 such that, when overlapping with a connector implant 3 aligned roughly perpendicular thereto (see FIG. 8), a section always remains accessible, allowing a further connector implant 3 to be immobilized with a tool (e.g., crimping tool) in the longitudinal direction L21 of the connecting element 21.

Figure 7:
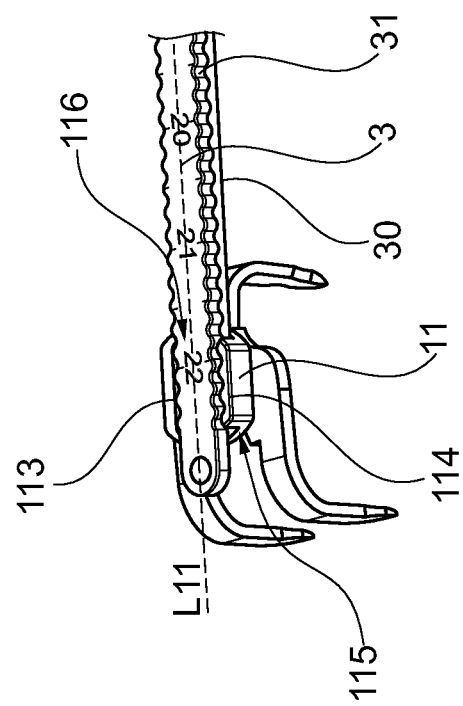
FIG. 7 is a perspective view of the embodiment of the first inventive implant from FIG. 1 in conjunction with a rod-shaped connector implant.

FIG. 7 shows a first implant 1, into the guide grooves 115, 116 of which is inserted a rod-shaped connector implant 3 that is displaceable along the longitudinal axis L11 of the connecting element 11.

The connector implant 3 has a dovetail-like cross-section structure with a base plate 30 which, in the direction perpendicular to the longitudinal axis L11 of the connecting element 11, engages with the grooves 115 and 116, and a top plate 31 of narrower cross-section in the direction perpendicular to the longitudinal axis L11 of the connecting element 11. The width of the top plate is slightly less than the distance between the free ends 1130 and 1140 of the first projection 113 and/or the second projection 114. However, should the connector implant 3 be immobilized by means of a tool in a specific position in the longitudinal direction L11, the distance between the first projection 113 and second projection 114 is reduced, such that the tooth structures formed on the free ends 1130 and 1140 of the first projection 113 and/or the second projection 114, engage with corresponding complementary tooth structures 310 and 311 formed on the outer sides of the top plate. The complementary tooth structures 310, 311 are directed outward and one of each of the tooth structures lies opposite the first projection 113 and/or the second projection 114. In this way, accurate relative positioning and immobilization of the connector implant 3, relative the first implant 1, is possible.

The force and direction of force exerted by the tool during immobilization is shown in FIG. 2 by the arrows F1 and −F1. Similarly, a connector implant 3 can be connected to a second connecting element 21 of the second implant 2.

Figure 8:
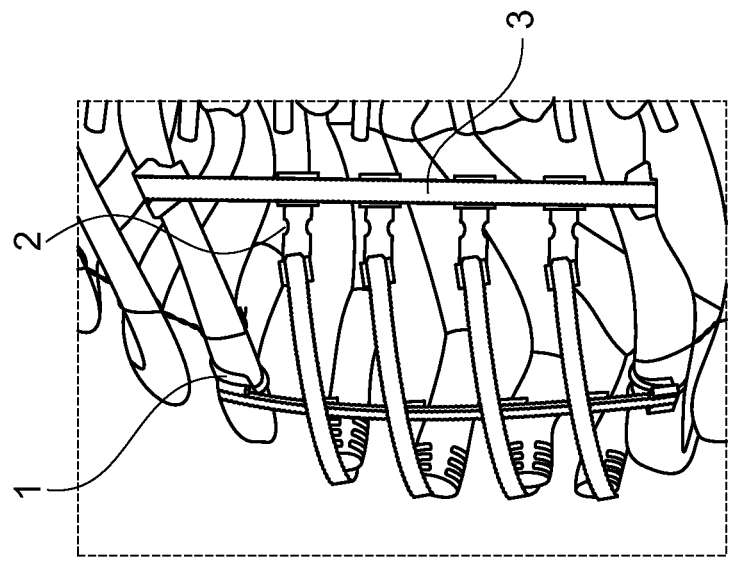
FIG. 8 is a perspective view of an example of thoracic stabilisation with the aid of the inventive implants.

FIG. 8 shows an application, wherein first implants 1 in accordance with the invention, second implants 2 in accordance with the invention, and connector implants 3 are used.

The connector implants 3 are immobilized to connecting elements of the implants 1 and 2. The illustration shows a further possibility afforded by the invention, namely "vertical stabilisation" parallel with the sternum or spine in indications for which there is no rib (e.g., Poland's syndrome) or, following a tumour removal (extremely close to the sternum or spine), the end piece of a rib had to be removed. The thorax model depicts (double) vertical stabilisation close to the spine with central defect, using four horizontal implant bridges. In the end sections, the bridging is attached and/or firmly clamped to the ends of the ribs by means of first implants 1 in accordance with the invention. The other end of the horizontal bridging is attached to a vertical bridging by means of second implants 2 in accordance with the invention. This creates a solid lattice structure, which nonetheless permits functional movements of the chest due to the rotatable connecting elements of the implants 1 and 2.

The invention claimed is:

1. A first implant for attaching the first implant to a tubular bone, in particular a rib bone, the first implant comprising:
   a clamp having a fillet and prongs extending from the fillet; and
   a first connecting element configured to connect the first implant to a connector implant, the clamp and the connecting element being connected to be rotatable relative to each other about an axis.

2. The first implant according to claim 1, wherein the implant has a connector which creates the rotatable connection between the clamp and the first connecting element.

3. The first implant according to claim 2, wherein one or more of the clamp and the connecting element have an opening, through which is guided at least a section of the connector to form an axis of rotation.

4. The first implant according to claim 2, wherein the connector is configured such that the fillet is configured to be immobilized in any angular alignment relative to the connecting element.

5. The first implant according to claim 2, wherein the connector is configured such that the connecting element retains a rotatable connection to the fillet while a connector implant is immobilized on the connecting element.

6. The first implant according to claim 2, wherein the fillet has a longitudinal axis and the prongs include at least a first prong, a second prong, and a third prong, the prongs extending from the fillet transversely to the longitudinal axis, the first prong and the third prong being disposed relative to the longitudinal axis on a first side of the fillet, the second prong being disposed relative to the longitudinal axis on a second side of the fillet, the prongs being disposed in a staggered arrangement opposite each other relative to the longitudinal axis.

7. The first implant according to claim 1, wherein the fillet has a longitudinal axis and the prongs include at least a first prong, a second prong, and a third prong, the prongs extending from the fillet transversely to the longitudinal axis, the first prong and the third prong are being disposed relative to the longitudinal axis on a first side of the fillet, the second prong being disposed relative to the longitudinal axis on a second side of the fillet, the prongs being disposed in a staggered arrangement opposite each other relative to the longitudinal axis.

8. The first implant according to claim 7, wherein the prongs are disposed in a staggered arrangement such that the prongs are laterally offset from each other.

9. The first implant according to claim 7, wherein sections of the prongs connected to the fillet extend transversely and/or perpendicularly outwards, relative to the longitudinal axis.

10. The first implant according to claim 7, wherein the resistance to bending of the prongs disposed at the first side of the fillet and gripped jointly by a tool during the attachment process corresponds to the resistance to bending of the prong disposed at the second side of the fillet and gripped jointly by a tool during the attachment process.

11. The first implant according to with claim 1, wherein one or more of the first element and the second connecting element has a base body, with a guide surface, a guide bar which extends upward from the guide surface along at least a section of a first side of the connecting element, and a second guide bar which extends upward from the guide surface along at least a section of a second side of the connecting element.

12. The first implant according to claim 11, wherein one or more of the first connecting element and the second connecting element has a first projection, which extends away from the first guide bar in the direction of the second guide bar, and a second projection, which extends away from the second guide bar in the direction of the first guide bar.

13. The first implant according to claim 12, wherein a free end of the first projection which faces the second guide bar has a first tooth-like contour, and/or a free end of the second projection which faces the first guide bar has a second tooth-like contour.

14. A first implant for attachment of the first implant to a tubular bone, especially a rib bone, the first implant comprising:
   a clamp including
      a fillet which has a longitudinal axis, and
      at least a first prong, a second prong, and a third prong, the prongs extending from the fillet transversely to the longitudinal axis, the first prong and the third prong being disposed relative to the longitudinal axis on a first side of the fillet, the second prong being disposed relative to the longitudinal axis on a second side of the fillet, the prongs being disposed in a staggered arrangement, relative to the longitudinal axis.

15. The first implant according to claim 14, wherein the prongs are disposed in a staggered arrangement such that the prongs are laterally offset from each other.

16. The first implant according to claim 14, wherein sections of the prongs connected to the fillet extend transversely and/or perpendicularly outwards, relative to the longitudinal axis.

17. The first implant according to claim 14, wherein the resistance to bending of the prongs disposed at the first side of the fillet and gripped jointly by a tool during the attachment process corresponds to the resistance to bending of the prong disposed at the second side of the fillet and gripped jointly by a tool during the attachment process.

* * * * *